United States Patent [19]
Schultz

[11] Patent Number: 5,868,750
[45] Date of Patent: Feb. 9, 1999

[54] ORTHOPEDIC PIN INSERTION TOOL

[75] Inventor: Richard J. Schultz, Hudson, Ohio

[73] Assignee: Spectrum Surgical Instruments, Inc., Cleveland, Ohio

[21] Appl. No.: 963,435

[22] Filed: Nov. 3, 1997

[51] Int. Cl.⁶ .................................................. A61B 17/56
[52] U.S. Cl. ............................................................ 606/104
[58] Field of Search ............................... 606/104, 96, 97, 606/98, 86, 99, 100; 173/213

[56] References Cited

U.S. PATENT DOCUMENTS

| | | |
|---|---|---|
| 2,267,925 | 12/1941 | Johnston .................................. 606/104 |
| 3,718,340 | 2/1973 | Stewart .................................... 606/104 |
| 4,050,528 | 9/1977 | Foltz et al. ............................... 606/104 |
| 4,342,309 | 8/1982 | Eftekhar .................................. 606/104 |
| 4,441,563 | 4/1984 | Walton, II ................................ 606/104 |
| 5,496,327 | 3/1996 | Den Ouden et al. .................... 606/104 |

*Primary Examiner*—Guy V. Tucker
*Attorney, Agent, or Firm*—Vickers, Daniels & Young

[57] ABSTRACT

An orthopedic pin insertion tool is provided which can be used as a hand-driven pin insertion tool or a power-driven pin insertion tool. The tool comprises a chuck and a chuck extension with a central passage which can be either stopped or continuous.

9 Claims, 2 Drawing Sheets

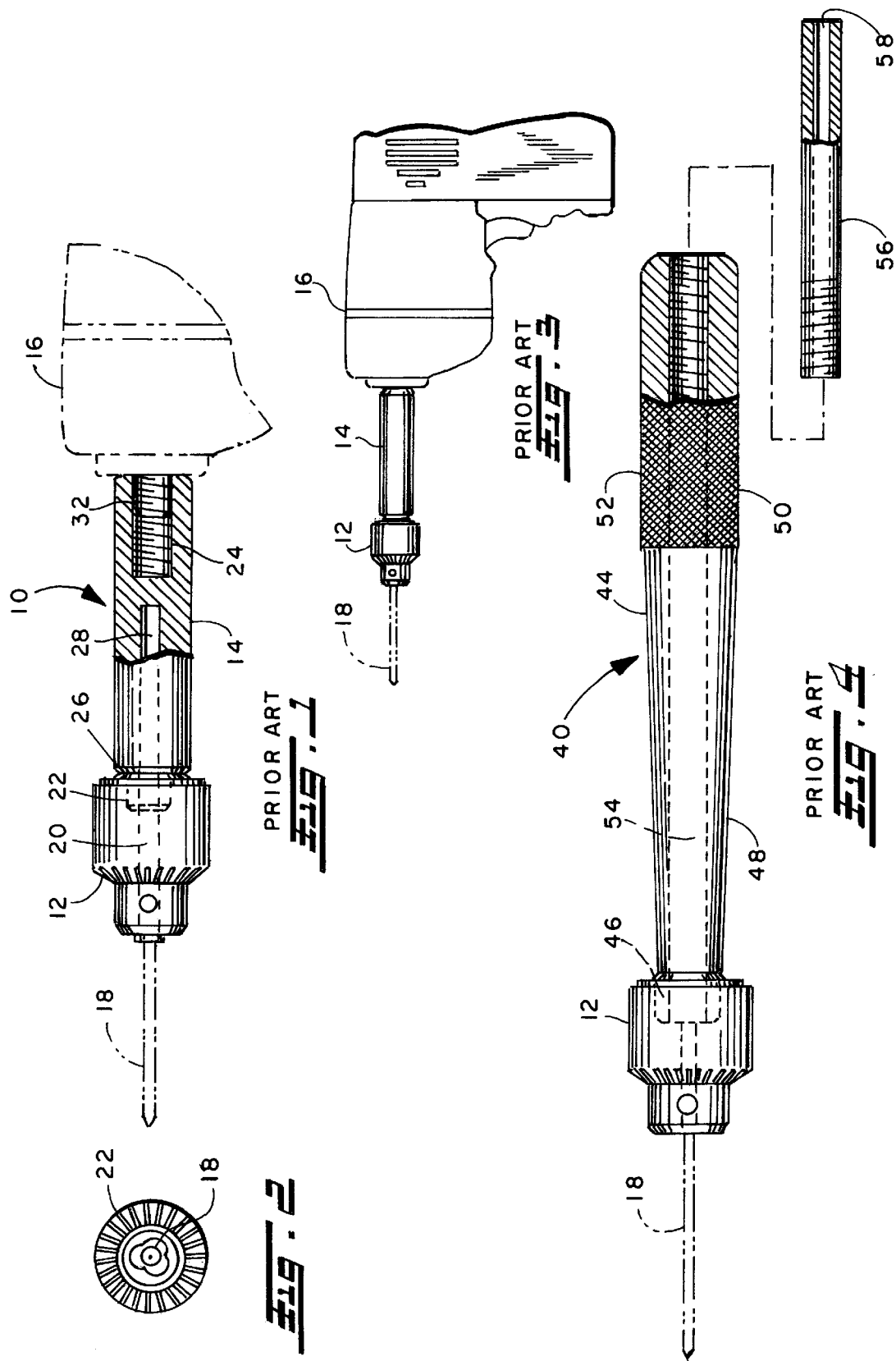

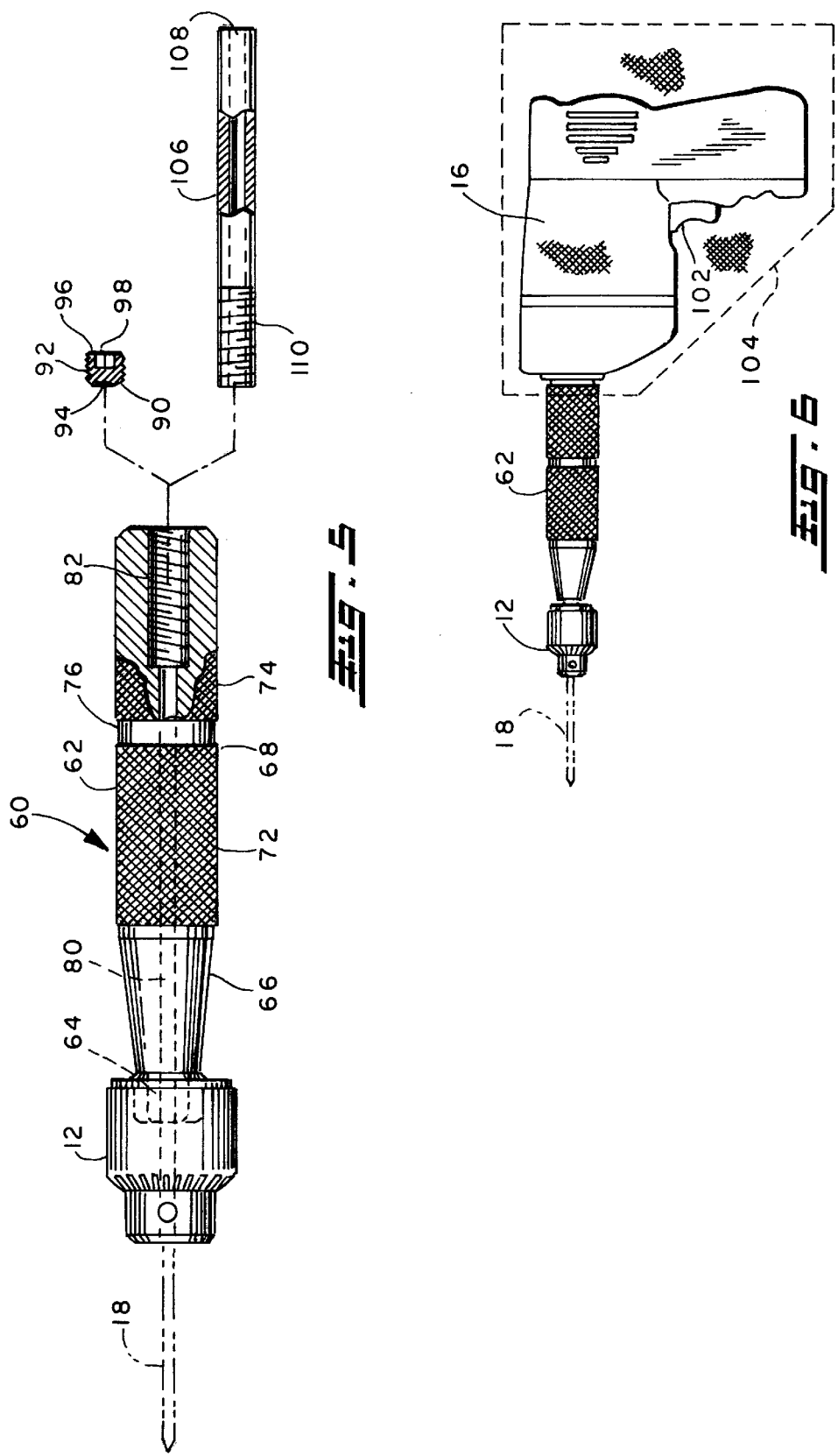

ORTHOPEDIC PIN INSERTION TOOL

BACKGROUND OF THE INVENTION

The present invention relates to orthopedic pin insertion tools of the type used to insert pins in bones to aid healing.

Veterinarians are often called upon to reset broken bones or perform surgical procedure in which bone structure is altered. These procedures and other procedures sometimes involve the insertion of a pin into the bone structure to immobilize portions of the bone with respect to one another or otherwise aid healing or provide structural support. Pins are available in a variety of diameters and with various tip designs. Some pins have smooth tips while others have partially threaded tips to aid in insertion and retention. Conventionally, pins are inserted with either a power tool or hand chuck. A hand chuck consists of standard chuck as one would see on a household power drill connected coaxially to a handle having a passage along its axis. An extension is sometimes provided on the handle at the end opposite the chuck. This entire assembly is sterilized, the pin is sterilized and the pin is inserted into the hand chuck with portions extending forward from the chuck and the rest being contained within the chuck and the handle and extension attached to the chuck. The chuck is tightened with a chuck key and the surgeon can then insert the pin by guiding it, turning it and applying pressure with the handle attached to the chuck. When the pin is properly positioned, the chuck is loosened, the tool removed, and the remaining pin cut-off. The axis of the chuck, the handle and the extension are all hollow providing an axial passage through the entire ensemble. This allowed the hand chuck to be used with long pin blanks.

Alternatively in the prior art, a low speed power drill was used to insert pins. The drill motor was provided with a removable extension which could be attached to the power output stud of the drill motor. The extension was in turn attached to a chuck. The extension had a blind passage extending along the axis of the extension coaxial with axis of the chuck. The extension passage had to be blind to protect the pin from the drill motor which could not be sterilized with conventional steam sterilization. A sterile shroud was placed around the drill motor, the sterile extension and chuck attached to the drill motor and the sterile pin inserted. The drill motor could then be used to guide, rotate and apply pressure to the pin inserting it as desired by the surgeon. When the pin was at the desired location, the chuck could be loosened, and the drill motor chuck assembly removed from the pin. The pin was then cut-off and the surgeon proceeded.

One cannot conveniently sterilize an electric drill motor. Therefore, prior art extensions for use with a drill motor had an aperture on one end to connect with the drill motor and a passage on the other end allowing intrusion of the pin into the extension. These two passages were not connected but were isolated one from the other. The extension to be attached to the drill motor was fabricated to close tolerances and shorter than the handle used with a hand chuck. This was necessary to prevent wobbling and to keep the pin coaxial and under control by the electric drill motor. The extension usable with an electric drill motor was generally smooth so as not to snag things. The extension could not be easily gripped and turned as could a hand chuck extension. Thus, persons purchasing pin insertion tools had to choose to buy either a hand chuck or a power chuck or both. One could not buy a tool capable of both applications.

SUMMARY OF THE INVENTION

In accordance with the present invention, an orthopedic pin insertion tool is provided comprising a chuck, a chuck extension having a passage, a removable passage stop, and a rear aperture adapted to accept either an electric drill motor or a passage extension tube.

Further in accordance with the invention, the passage stop is threaded with threads matching the threads provided on the inside surface of at least the rear portion of the passage whereby the passage stop may be easily fixed in place or removed.

Yet further in accordance with the invention, the chuck extension is generally cylindrical and has a easily gripped outer surface whereby the chuck, the extension and the pin they hold can be accurately positioned and easily rotated.

Still further in accordance with the invention, the chuck extension is fabricated from a single piece of metal which is easily sterilizable and kept clean.

Still further in accordance with the invention, the chuck extension is provided with a threaded forward end having external threads of a standard characteristic and a threaded rearward opening into the passageway having threads of a standard characteristic matching the threads on the forward end.

Yet further in accordance with the invention, the threads on the forward end and rear end of the aperture are of a standard size selected to engage the threads on the standard chuck and drill motor.

Yet further in accordance with the invention, the threads on the forward end and rear aperture of the chuck invention made with the standard threads used on a ¼" chuck e.g. ⅜-24 threads.

The principal object of the invention is to provide an orthopedic pin insertion tool which may be used as a hand-driven pin insertion tool without a drill motor or as a power drill insertion tool using a drill motor.

It is a further object of the invention to provide a combination hand-driven or power-driven pin insertion tool which is easily sterilizable and which provides for isolation of a pin from non-sterile portions in either in the hand-driven or power-driven mode of operation.

It is still a further object of the present invention to provide an orthopedic pin insertion tool allowing a surgeon to first buy a hand-driven unit and then later supplement it with a power drive unit as the occasion demands.

It is a further object of the invention to provide an improved orthopedic pin insertion tool having easy grip ergonomic characteristics for surgeons having smaller hands.

It is yet another object of the invention to provide an orthopedic pin insertion tool which can be used as a hand orthopedic pin insertion tool or a power-driven pin insertion tool which will not wobble and will maintain a straight axis.

It is yet another object of the present invention to provide an orthopedic pin insertion tool which is easily changed from the hand driven mode to the power driven mode.

It is still another object of the present invention to provide an orthopedic pin insertion tool which can have the characteristics of an open passageway for hand use or a closed passageway for power use.

It is still another object of the present invention to provide an orthopedic pin insertion tool which can be inexpensively purchased by a beginning surgeon and upgraded to a power pin insertion tool as the requirements of the practice grow.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof and wherein:

FIG. 1 shows the construction of a conventional power pin insertion tool, partially sectioned;

FIG. 2 shows a front view of the end of the pin insertion tool of FIG. 1 showing the face of the chuck;

FIG. 3 shows the power pin insertion tool of FIG. 1 and FIG. 2 in a somewhat reduced scale as connected to a drill motor;

FIG. 4 shows a conventional hand pin insertion tool partially in section;

FIG. 5 shows the various elements of the pin insertion tool of the present invention except for the drill motor and drill motor shroud, some elements shown partially in section; and, FIG. 6 shows the pin insertion tool of FIG. 5 as assembled to an electric drill motor covered by a shroud.

DESCRIPTION OF THE PREFERRED EMBODIMENTS

Referring now to the drawings where the showings are made for the purposes of illustrating a preferred embodiment of the invention only and not for the purposes of limiting the invention, FIG. 1 shows the elements of a prior art power orthopedic pin insertion tool 10. The pin insertion tool comprises a chuck 12, a chuck extension 14 and an electric hand drill 16. The chuck 12 is a conventional design available from the Jacobs Company and others. Advantageously, the chuck is available in a stainless steel model making it easy to maintain and sterilize. In the embodiment, a standard commercially available Jacobs brand ¼ inch chuck is used. The chuck will accommodate pins up to ¼ inch in diameter and can be easily tightened on such pins 18 in a chuck passage 20 through the center of the chuck. The chuck is provided with threads 22 on the rear end of the passage 20. The commercially available chuck has ⅜-24 threads.

The chuck extension 14 is fabricated from a single piece of metal and is generally cylindrical. The chuck extension is provided with a rearwardly facing blind threaded hole 24 which is about one inch deep. The chuck extension 14 is also provided with a ⅜-24 outside threaded forward stud portion 26 which is approximately ½ inch long. The forward stud portion 26 engages the threads 22 in the chuck 12. A forward passage 28 extends from the front face of the forward stud portion 26 into the body of the extension 14. The forward passage 28 is cylindrical, about a ¼ inch in diameter and about 2¼ inch long. The forward passage is blind. It has an opening on only one end. The extension 14, the rearward blind threaded hole 24, the forward stud portion 26, and the forward passage 28 are all generally cylindrical and coaxial.

The electric hand drill, shown more fully in FIG. 3 is conventional and commercially available. Appropriate hand drills include battery powered hand drills designed to accept standard ¼ inch or ⅜ inch chuck. Numerous models are available which will accommodate the controlled low speed operation needed for orthopedic pin insertion. The drill 16 is connected to the chuck extension 14 by means of a threaded output shaft 32 having ⅜-24 threads which engage the rearward blind threaded hole 24.

A fabric or other sheet material shroud (not shown) is used to cover electric drill 16. Thus, when the tool is to be used, a selected pin 18, the chuck 12, the extension 14, and the shroud are sterilized. The shroud is placed over the electric hand drill and the extension 14, chuck 12 and pin 18 assembled thereto. The pin 18 can then be inserted with only sterile surfaces presented to the wound or surgery site.

The isolation of the forward passage 28 from the blind threaded hole 24 prevents the pin 18 from contacting the non-sterile drill 16 and contaminating the process.

FIG. 4 shows a hand orthopedic pin insertion tool 40. The chuck 12 used with the hand orthopedic pin insertion tool 40 is identical in all respects to the chuck 12 used with the power orthopedic pin insertion tool 10. A chuck extension 44 is provided with a forwardly extending threaded stud 46 which engages and locks to the chuck 12. The stud 46 is about ½–⅝ inch long. Chuck extension 44 has a tapered portion 48 and a cylindrical grip portion 50. The tapered portion 48 is about ⅝ inch in diameter at the chuck end and almost one inch in diameter where it joins the cylindrical grip 50. The tapered portion is about 2½ inches long and the grip portion 50 is about 2¼ inches long and one inch in diameter. The grip portion 50 is provided with a knurled surface 52. The chuck extension 44 has a cylindrical central passage 54 extending its entire length. The central passage 54 is about ¼ inch in diameter and is provided with ⅜-24 threads at its rearward end. A passage extension 56 is a metal tube having an inside diameter of approximately ¼ inch and ⅜-24 threads on the exterior of one end extending about ¾ inch along the tube. The passage extension 56 can be threaded into the rearward threaded end of the chuck extension 42 to provide an additional length of passage 50 to protect long pins 18. When thus assembled, the pin 18, the chuck 12, the chuck extension 44, the passage extension 56, and the central passage all share the same axis. The threads on the rear end of the central passage do not need to have great precision of axis as the chuck extension 44 is turned by hand power applied to the grip 50. The threads only perform the task of holding passage extension 56.

The central passage 54 through the hand orthopedic pin insertion tool 40 is continuous from one end to the other. The pin 18 can pass completely through the extension 44 if so desired.

Referring now to FIG. 5, the combination orthopedic pin and insertion tool 60 of the present invention is shown. A pin 18 shown in phantom extending from a chuck 12. The pin 18 and chuck 12 are identical to those described hereinabove and are commercially available.

A chuck extension 62 comprises a forwardly extending stud 64 having ⅜-24 threads which engage the chuck 12. The chuck extension has a short tapered portion 66 and a cylindrical grip portion 68. The stud 64 is about ½ inch long. The tapered portion 66 is about 2¼ inches long and tapers from a ⅝ inch diameter at the stud 64 to a ⅞ inch diameter at the cylindrical grip 68. The cylindrical grip is about 3¾ inches long and is provided with two knurled bands 72, 74 separated by a ¼ inch smooth band 76. The entire grip portion 68 is about ⅞ inch in diameter. A central passage 80 is provided through the entire length of the chuck extension 62. ⅜-24 threads 82 are provided in the rearward end of the central passage 80. The rest of the central passage 80 is about ¼ inch in diameter. The chuck 12, chuck extension 62, stud 64, central passage 80, and threads 82 are all generally cylindrical and coaxial. The threaded portion of the central passage 80 and the threaded stud 64 are precisely coaxial to prevent wobble when the tool is used on the electric drill.

A passage stop 90 is generally cylindrical with ⅜-24 threads provided over its entire cylindrical surface. The forward end 94 has a cupped face and the rearward end 96 of the passage stop 90 is provided with a six-sided aperture 98 which will mate with a standard size Allen head driver. The passage stop can be easily inserted in the threaded portion 82 of the central passage 80 to a depth of about one inch. This leaves room in the threaded portion for the attachment of an electric drill which will then be completely isolated from the forward portion of the passage 80 by the passage stop 90. The use of the invention is illustrated in FIG. 6 showing the pin 18 supported in the chuck 12 which is in turn attached to the chuck extension 62. The chuck extension can be driven by gentle pressure on the trigger 102 of the electric hand drill 16. The electric hand drill 16 is isolated from the rest of the tool by a fabric or film shroud 104 which completely surrounds the hand drill but provides an aperture for the chuck extension to engage the hand drill. In this manner, the hand drill 16 is isolated on the outside by the shroud 104 and the threaded output shaft 32 of the electric drill is isolated from the pin 18 by the passage stop 90. Because the threads 82 and the central passage and the threads on the stud 64 are precisely coaxial, the chuck 12 and the pin 18 are coaxial with the output of the hand drill and wobble is avoided.

Alternatively, the passage stop 90 can be removed from the threaded end portion 82 at the central passage 80. A passage extension 106 having a ¼ inch diameter inner passage 108 can be attached to the chuck extension 62. ⅜-24 threads 110 are provided over the first ¾ inch of the passage extension 106. The threads 110 are screwed into the threads 82 of the central passage 80 in the chuck extension 72. The overall length of the passage extension 106 is four inches. When fully threaded into the chuck extension 62, it extends ¾ inch so that the length of the chuck extension 62 and passage extension together from the rearward face of the chuck 12 to the end of the end of the extension is 8¼ inches. Because the chuck extension 62 is shorter than a conventional hand chuck extension 44 and smaller in diameter, it is significantly lighter. Slightly longer protection for pin 18 is provided by the present invention with less weight.

A ⅜-24 stainless steel hollow cup point set screw can be used advantageously as the passage stop 90. Such set screws are commercially available and the cup point provides a positive stop and centering function for the end of a pin 18 pushed against it.

The invention has been described with reference to a preferred embodiment, obviously, modifications and alterations will occur to others upon the reading and understanding of this specification and it is intended to include such modifications and alterations insofar as to come within the scope of the appended claims or the equivalents thereof.

Having thus described the invention, it is so claimed:

1. An orthopedic pin insertion tool comprising:
   a chuck having an axis of rotation and a passage along said axis of rotation, said chuck being adapted to grip an orthopedic pin positioned on said chuck axis;
   a chuck extension having an axis, an extension passage along said axis, a forward end adapted to engage said chuck with said extension axis and said chuck axis being coaxial, a rearward end, said extension passage extending on said axis between said forward end and said rearward end and being threaded adjacent said rearward end and adapted to be mounted on an electric motor; and,
   a removable passage stop positioned in said extension passage isolating said forward end from said rearward end.

2. The tool of claim 1, wherein said passage stop is threaded.

3. The tool of claim 2, wherein said extension is generally cylindrical and has a maximum diameter of about ⅞ inch.

4. The tool of claim 2, wherein said threaded passage stop mates with said threaded extension passage adjacent said rearward end.

5. The tool of claim 4, wherein said passage stop is a set screw having a cupped forward facing surface.

6. The tool of claim 1, wherein said chuck extension additionally comprises a grip enhancing outer surface.

7. The tool of claim 6, wherein said grip enhancing outer surface is a texture.

8. The tool of claim 7, wherein said texture is a knurled texture.

9. An orthopedic pin insertion tool comprising:
   a chuck having an axis of rotation and a passage along said axis of rotation, said chuck being adapted to grip an orthopedic pin positioned on said chuck axis;
   a chuck extension having an axis, an extension passage along said axis, a forward end adapted to engage said chuck with said extension axis and said chuck axis being coaxial, a rearward end, said extension passage being threaded adjacent said rearward end and adapted to be mounted on an electric motor; and,
   a removable threaded passage stop positioned in said extension passage, and said threaded passage stop is a set screw having a cupped forward facing surface and mates with said threaded extension passage adjacent said rearward end.

* * * * *